United States Patent [19]

Oesterlin

[11] 4,351,944

[45] Sep. 28, 1982

[54] IMPROVED PROCESS FOR PREPARING 3-(4-PYRIDINYL)ANILINE

[75] Inventor: Rudolf Oesterlin, East Greenbush, N.Y.

[73] Assignee: Sterling Drug Inc., New York, N.Y.

[21] Appl. No.: 266,667

[22] Filed: May 26, 1981

Related U.S. Application Data

[63] Continuation-in-part of Ser. No. 103,191, Dec. 13, 1979, abandoned.

[51] Int. Cl.³ .......................................... C07D 213/38
[52] U.S. Cl. ...................................................... 546/329
[58] Field of Search .......................................... 546/329

[56] References Cited

U.S. PATENT DOCUMENTS 4,026,900  5/1977  Gelotte et al. ..................... 546/329
4,075,217  2/1978  Gelotte et al. ..................... 546/329

OTHER PUBLICATIONS

Newman and Hung [J. Org. Chem. 38, 4073–4074 (1973)].

*Primary Examiner*—Henry R. Jiles
*Assistant Examiner*—Bernard Dentz
*Attorney, Agent, or Firm*—Robert K. Bair; B. Woodrow Wyatt; Paul E. Dupont

[57] ABSTRACT

An improved method of preparing 3-(4-pyridinyl)aniline comprises heating 3-(4-pyridinyl)-2-cyclohexen-1-one oxime with an excess each of acetic anhydride and anhydrous phosphoric acid, distilling off the acetic acid by-product and excess acetic anhydride, adjusting the pH of the reaction mixture to about 5 to 9 with concentrated aqueous alkali, extracting N-acetyl-3-(4-pyridinyl)aniline from the concentrated aqueous phosphate salt solution with a lower-alkanol, and hydrolyzing the N-acetyl-3-(4-pyridinyl)aniline.

5 Claims, No Drawings

IMPROVED PROCESS FOR PREPARING 3-(4-PYRIDINYL)ANILINE

CROSS-REFERENCE TO RELATED APPLICATION

This application is a continuation-in-part of copending application Ser. No. 103,191, filed Dec. 13, 1979 and now abandoned.

BACKGROUND OF THE INVENTION (a) Field of the Invention

This invention relates to an improved method for preparing 3-(4-pyridinyl)aniline, an intermediate for preparing rosoxacin, an antibacterial agent.

(b) Description of the Prior Art

Gelotte et al U.S. Pat. Nos. 4,026,900 and 4,075,217 disclose, and 4,075,217 claims, the process of heating the oxime of 3-(4-pyridinyl)-2-cyclohexen-1-one with an acetylating agent to produce the resulting O-acetyl oxime and then heating the O-acetyl oxime under acidic conditions, preferably in the presence of a strong mineral acid. The acetylation and subsequent heating steps were preferably run in combination by heating the oxime with acetic acid, acetic anhydride and hydrogen halide, preferably hydrogen chloride gas. The reaction was run in the range of about 80° to 140° C., preferably 100° to 120° C. The N-acetyl-3-(4-pyridinyl)aniline was then hydrolyzed to produce 3-(4-pyridinyl)aniline, an intermediate for preparing rosoxacin a known antibacterial agent.

Newman and Hung [J. Org. Chem. 38, 4073–4074 (1973)] showed the conversion of certain oximes of α-tetralones (7-methyl- and 7-chloro-α-tetralones) to the corresponding N-(1-naphthyl)acetamides by heating the oxime in acetic anhydride and anhydrous phosphoric acid at 80° C. for thirty minutes. Unsuccessful results due to side-reactions resulted using these reaction conditions with the oxime of 6-methoxy-α-tetralone. Phosphorus pentoxide was used to prepare the anhydrous phosphoric acid.

SUMMARY OF THE INVENTION

The invention relates to an improvement in the process for converting 3-(4-pyridinyl)-2-cyclohexen-1-one oxime to 3-(4-pyridinyl)aniline, the improvement which comprises heating said oxime with an excess each of acetic anhydride and anhydrous phosphoric acid, distilling off the acetic acid by-product and excess acetic anhydride, adjusting the pH of the reaction mixture to a range of about 5 to 9, extracting N-acetyl-3-(4-pyridinyl)aniline from the reaction mixture with a lower-alkanol, preferably ethanol, and then hydrolyzing the N-acetyl-3-(4-pyridinyl)aniline. The improvement is based on the use of phosphoric acid instead of hydrogen chloride in the first step, use of the pH-adjusting step and the use of a water-soluble solvent, e.g., a lower-alkanol, to extract the N-acetyl intermediate from the concentrated aqueous inorganic phosphate solution.

DETAILED DESCRIPTION INCLUSIVE OF PREFERRED EMBODIMENTS

This invention resides in an improvement in the process for preparing 3-(4-pyridinyl)aniline by acetylating 3-(4-pyridinyl)-2-cyclohexen-1-oxime to produce the corresponding O-acetyl oxime, heating the latter under acidic conditions to produce the N-acetyl-3-(4-pyridinyl)aniline and hydrolyzing the N-acetyl compound, said improvement which comprises heating 3-(4-pyridinyl)-2-cyclohexen-1-one oxime with an excess each of acetic anhydride and anhydrous phosphoric acid, distilling off the acetic acid by-product and excess acetic anhydride, adjusting the pH of the reaction mixture to about 5 to 9 with concentrated aqueous alkali, extracting N-acetyl-3-(4-pyridinyl)aniline from the concentrated aqueous inorganic phosphate salt solution with a lower-alkanol and hydrolyzing the N-acetyl-3-(4-pyridinyl)aniline under alkaline conditions.

In using phosphoric acid instead of hydrogen chloride gas (used by Gelotte et al.), a pH-adjusting step and a lower-alkanol in the extraction step, the improved process provides a convenient one-pot procedure that is more adaptable to and hence preferred in large scale production when compared with the prior art procedure of Gelotte et al. It overcomes the disadvantages of using hydrogen chloride gas which is poorly soluble in the hot reaction mixture thereby requiring the use of a large quantity of the acidic gas and further requiring cumbersome means for neutralizing or otherwise taking up the excess hydrogen chloride gas emanating from the reaction mixture, a decided problem particularly in large scale production. Use of the simplified pH adjustment and extraction steps of applicants' process provides a convenient means of separating the N-acetyl-3-(4-pyridinyl)aniline from the reaction mixture. Use of the water-miscible lower-alkanol, especially ethanol, as the solvent to extract the N-acetyl compound from the concentrated aqueous inorganic phosphate salt solution is a non-obvious departure from the teachings of Gelotte et al., which require successive dilutions of the reaction mixture first with water followed by 35% aqueous sodium hydroxide to make the mixture definitely basic and then enough ethanol to make the mixture homogeneous, thereby resulting in inconveniently large volumes. The extraction step of the instant process improvement conveniently results in an upper layer of lower-alkanol containing the N-acetyl compound and a heavier aqueous lower layer containing inorganic phosphate salts, which is readily drawn off from the mixture, thereby reducing its volume. The N-acetyl compound in alkanol solution is then hydrolyzed directly to produce in very good yield the intermediate 3-(4-pyridinyl)aniline, which is ready for use in the synthesis of rosoxacin without further purification.

The anhydrous phosphoric acid used in the process was prepared by dehydrating 85% phosphoric acid by reacting it with acetic anhydride.

In a preferred embodiment the first step of the process was run using about 7 to 10 mole-equivalents of acetic anhydride and about 3 to 10 mole equivalents of anhydrous phosphoric acid per mole-equivalent of oxime and heating the reactants at about 90° to 120° C., preferably 95° to 120° C. The first step of the process also can be run using more acetic-anhydride and anhydrous phosphoric acid, viz., up to about 15–20 mole-equivalents of each per mole-equivalent of oxime, but to no particular advantage.

The pH adjustment step is carried out using concentrated aqueous alkali, preferably about 35% aqueous sodium hydroxide solution. The pH adjustment can be carried to a range of about 5 to 9, that is, to a slightly acidic pH range of about 5 to 6 or to a slightly alkaline pH range of about 8 to 9, preferably the former.

The extraction step is carried out by stirring well with a lower-alkanol, preferably ethanol, the concentrated aqueous inorganic phosphate salt solution containing N-acetyl-3-(4-pyridinyl)aniline and drawing off the heavier layer of aqueous inorganic phosphate salt solution from the lighter layer of lower-alkanol containing the extracted N-acetyl-3-(4-pyridinyl)aniline. The extraction was carried out at about 50°–80° C.; the drawing off of the heavier aqueous phosphate salt solution was done with its temperature ranging from about 30° to 60° C., preferably 50° to 60° C. if the pH of the aqueous solution is slightly alkaline (8 to 9) and at about 30°–40° C. if its pH is slightly acidic (5 to 6). Other lower-alkanols, in addition to the preferred ethanol, include methanol and isopropyl alcohol.

The hydrolysis step is conveniently run using an aqueous alkali metal hydroxide, preferably sodium hydroxide.

The following examples will further illustrate the invention without, however, limiting it thereto.

EXAMPLE 1

3-(4-Pyridinyl)aniline, alternatively named 3-(4-pyridinyl)benzeneamine - Anhydrous phosphoric acid was prepared by the addition of 1,020 g. (10 moles, d 1.082, 940 ml.) of acetic anhydride to 540 g. (4.68 moles, d 1.7, 320 ml.) of vigorously stirred 85% phosphoric acid over 20 minutes maintaining the temperature near 50° C. with occasional cooling. To the clear warm solution was added 188 g. (1 mole) of 3-(4-pyridinyl)-2-cyclohexen-1-one oxime in one portion. The initially clear, yellow solution was heated on a steam bath to about 95° C. where the steam was shut off. At this point the reaction mixture started to separate into two layers, eventually forming a mobile water-white upper layer and a yellow-brown viscous gum. The internal temperature of the reaction mixture very gradually increased to about 110°–120° C. As soon as the temperature started to decrease, steam was again applied for 90 minutes. The generated acetic acid (colorless upper layer, 650–700 ml.) was then removed by vacuum distillation followed by removal of the excess acetic anhydride in vacuo. The continuously stirred and heated viscous residue was readily dissolved in 500 ml. of warm water. The clear dark solution was treated gradually and with occasional cooling with about 800 ml. of 35% aqueous sodium hydroxide at 60°–80° C. to a weakly basic pH (8–9). The 35% aqueous sodium hydroxide solution serves as concentrated aqueous alkali for neutralizing the excess phosphoric acid. Some precipitated solid was solubilized by the addition of 500 ml. of ethanol to the stirred mixture and heating it to 80° C. The ethanol further serves to extract N-acetyl-3-(4-pyridinyl)aniline as an upper layer from the concentrated aqueous inorganic phosphate salt solution. The colorless viscous lower layer containing said phosphate salts was drawn off while hot (1 l., 1,430 g.); it solidified at ambient temperature. To the remaining dark solution was added 320 ml. of 35% aqueous sodium hydroxide and the resulting two-phase reaction mixture was heated at reflux overnight (about 16 hours) to hydrolyze the N-acetyl-3-(4-pyridinyl)aniline. The dark, homogeneous solution was cooled to 5° C. The crystallized solid was filtered, pressed well and then washed with the minimum amount (just enough to cover solid) of ice-methanol cooled 50% aqueous ethanol. To remove any remaining inorganic salts in the filter cake, the solid was washed exhaustively with warm water (about 35° to 50° C.). The residue was dried in vacuo at 60° C. to afford 134.5 g. (79%) of the desired product, 3-(4-pyridinyl)aniline, as a beige solid, m.p. 168°–171° C.; single spot on tlc (silica; $CHCl_3$: $CH_3OH$: i—$C_3H_7NH_2$ 90:5:5; UV).

It is contemplated that the process of Example 1 can be carried out using methanol or isopropyl alcohol in place of ethanol.

EXAMPLE 2

3-(4-Pyridinyl)aniline was prepared in comparable yield on a pilot plant scale using the same procedure, as follows: Acetic anhydride, 55 kg., was charged to the 30 gallon glass-lined reactor of a distillation unit. The phosphoric acid was added over one-half hour, with temperature rising to 100° C. The solution was heated to 120° C. and the steam shut off. A solution of 14.6 kg. of oxime in 36 l. of acetic acid was added at a rate to maintain reflux but not cause distillation. Approximately ¾th of the solution was added over one and one-half hours resulting in a full kettle. Pressure steam (35–40 lbs.) was applied to begin distillation of acetic acid. After one-half hour, there was room in the kettle and the remaining oxime solution was added slowly, maintaining distillation. The clear acetic acid layer was distilled off at atmospheric pressure over two hours leaving a dark and viscous, but stirrable residue at 120° C. Vacuum was applied gradually to remove the remaining acetic acid and acetic anhydride, keeping the pot temperature over 100° C. With the residue stirring at 100° C., (heat off), 20 l. of water was added over 5 minutes. The temperature dropped to 85° C. but stirring was maintained. The kettle was cooled with water to 60° C., and 54 kg. of 35% aqueous sodium hydroxide was added over one-half hour, temperature 50°–65° C., the resulting pH being slightly acidic (about 5 to 6). Ethanol, 20 l., was added with stirring to extract the N-acetyl-3-(4-pyridinyl)aniline and the mixture cooled to 30° C. before being allowed to separate. A clear aqueous layer, 66 l., was drawn off and the very dark organic layer, 56 l., was transferred to a stainless steel kettle. 35% aqueous sodium hydroxide, 34 kg., was added to the kettle and the mixture was refluxed (83° C.) for 12 hours. The mixture was cooled from 60° to 5° C. before filtration. The dark solids were washed with 3×6 l. of cold 25% ethanol to give a tan product. The wet cake was slurried in 40 l. of water at 30° C. for one-half hour and refiltered. The solids were washed generously with water and dried 60° C./air/overnight. There resulted 10.08 kg., or 10080/77.8×170=76.3% of theory, of the tan product, 3-(4-pyridinyl)aniline, m.p. 165°–7° C.

I claim:

1. In the process for preparing 3-(4-pyridinyl)aniline by acetylating 3-(4-pyridinyl)-2-cyclohexen-1-one oxime to produce the corresponding O-acetyl oxime, and heating the latter under acidic conditions to produce N-acetyl-3-(4-pyridinyl)aniline and hydrolyzing the N-acetyl compound, the improvement which comprises heating 3-(4-pyridinyl)-2-cyclohexen-1-one oxime with an excess each of acetic anhydride and anhydrous phosphoric acid, distilling off the acetic acid by-product and excess acetic anhydride, adjusting the pH of the reaction mixture to about 5 to 9 with concentrated aqueous alkali, extracting N-acetyl-3-(4-pyridinyl)aniline from the concentrated aqueous phosphate salt solution with a lower-alkanol, and hydrolyzing the N-acetyl-3-(4-pyridinyl)aniline.

2. The process according to claim 1 where about 7 to 10 mole-equivalents of acetic anhydride and about 3 to 10 mole-equivalents of anhydrous phosphoric acid are used per mole-equivalent of oxime.

3. The process according to claim 2 where the reactants in the first step are heated at about 90° to 120° C.

4. The process according to claim 2 where the pH of the reaction mixture is adjusted to about 5 to 6.

5. The process according to claim 2 where the extraction step is carried out at 50° to 80° C. and ethanol is used as the extracting solvent.

* * * * *